(12) United States Patent
Riviere et al.

(10) Patent No.: US 6,235,282 B1
(45) Date of Patent: *May 22, 2001

(54) VACCINAL FLUID WATER-IN-OIL EMULSIONS CONTAINING A METABOLIZABLE OIL

(75) Inventors: Michel Emile Albert Riviere, Ecully; Claude Roulet, Venissieux, both of (FR)

(73) Assignee: Rhone Merieux, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/909,767

(22) Filed: Aug. 12, 1997

Related U.S. Application Data

(63) Continuation of application No. 08/331,543, filed as application No. PCT/FR94/00242 on Mar. 4, 1994, now abandoned.

(30) Foreign Application Priority Data

Mar. 8, 1993 (FR) .................................................. 93 02661
Dec. 7, 1993 (FR) .................................................. 93 14651

(51) Int. Cl.$^7$ ........................... A61K 39/00; A61K 39/38
(52) U.S. Cl. ................. 424/184.1; 424/1.11; 424/190.1; 424/191.1; 424/192.1; 424/193.1; 424/199.1; 424/200.1; 424/201.1; 424/278.1; 424/283.1; 514/785
(58) Field of Search ................................ 424/184.1, 1.11, 424/190.1, 191.1, 192.1, 193.1, 199.1, 200.1, 201.1, 278.1, 283.1; 514/785

(56) References Cited

U.S. PATENT DOCUMENTS

| | | | |
|---|---|---|---|
| 3,983,228 | * | 9/1976 | Woodhour et al. .................... 424/89 |
| 4,606,918 | * | 8/1986 | Allison et al. ......................... 424/88 |
| 4,770,874 | * | 9/1988 | Allison et al. ......................... 424/88 |
| 4,806,352 | * | 2/1989 | Cantrell et al. ........................ 424/92 |
| 5,422,109 | * | 6/1995 | Brancq et al. ..................... 424/184.1 |
| 5,424,067 | * | 6/1995 | Brancq et al. ..................... 424/184.1 |

FOREIGN PATENT DOCUMENTS

174377 * 3/1985 (JP) .
5-255112 * 10/1993 (JP) .

OTHER PUBLICATIONS

Edelman, Robert et al. Adjuvants, Intern. Review of Immunology, vol. 7, pp. 51–66, 1990.*

Coupland, David et al. The Evaluation of Ten Emulsifiers for Use with a Mineral Oil Adjuvant, Adjuvants for Agrichemicals, Chapter 43, pp. 449–461.*

* cited by examiner

Primary Examiner—Christopher L. Chin
Assistant Examiner—Bao-Thuy L. Nguyen
(74) Attorney, Agent, or Firm—Larson and Taylor

(57) ABSTRACT

Injectable water-in-oil emulsion possessing immunity adjuvant activity and which can be used in man and animals as vaccine or an immunological medicament comprising an oily phase comprising an oil , an aqueous phase and at least one emulsifier, wherein the oil of said oily phase is a substantially metabolizable oil or a mixture of substantially metabolizable oils and said emulsifiers or emulsifiers providing with said metabolizable oil a stable emulsion having immunity adjuvant activity and a viscosity of less than 400 mPa.s at 25° C.

41 Claims, No Drawings

VACCINAL FLUID WATER-IN-OIL EMULSIONS CONTAINING A METABOLIZABLE OIL

This application is a continuation of application Ser. No. 08/331,543 filed Jan. 17, 1995 filed as PCT/FR 94/00242 on Mar. 4, 1994 now abandoned.

The present invention mainly relates to entirely metabolizable injectable water-in-oil emulsions intended to stimulate the immune response induced by active principles, which may be viruses, bacteria, parasites or fractions of the latter, toxins, polysaccharides but also recombinant proteins, or else small antigen molecules, for example peptides, coupled to carrier molecules.

Knowledge restatement

Vaccination, by stimulating the immune defense system, is a means for the preventive control of infectious agents. Vaccines currently use as antigens either living microorganisms whose pathogenic power has been attenuated or killed microorganisms, or indeed even purified fractions from these microorganisms. The sub-units or inactivated vaccines very often contain an adjuvant substance which is intended to increase the immune response. The function of the adjuvant is to increase, on the one hand, the level of the humoral and cellular immune response and, on the other hand, the duration of this response. Consequently, the adjuvant makes it possible to reduce the number of injections and the antigen dose included in the vaccine, thus keeping the vaccination at an acceptable cost. In addition to the desired effect on the immune response, the adjuvant substances can induce local or general toxicity: inflammatory edema, abscess, fibrosis at the point of injection, pain, fever or stimulation of a hyper-sensitivity state. An adjuvant must be effective but must also be acceptable as regards toxicity.

Mention may be made, among the many immunity adjuvant substances, of gels derived from aluminum (hydroxide, phosphate), which are only used in human medicine, saponins, which are complex heterosides and which are employed in the veterinary field, and also emulsions which seem to be one of the most active excipients. In particular, emulsions containing mycobacteria in mineral oil and Arlacel A®, which is defined as a dianhydromannitol monooleate, as surface-active agents are widely used under the name of Freund's complete adjuvant for laboratory animal immunization. Nevertheless, the use of killed mycobacteria has two major drawbacks: local reactions at the point of injection are very significant and the animals are sensitized to tuberculin; this leads to this adjuvant being rejected in veterinary medicine. The same adjuvant without mycobacteria, known as Freund's incomplete adjuvant, is less poorly tolerated and is still widely used in laboratories for producing hyperimmune sera. However, emulsions prepared with the Freund adjuvants are very viscous and have little stability, which prevents their industrial development. Research into the substances responsible for the adjuvant effect of mycobacteria has led to the characterization of peptidoglycans (MDP) and glycolipids (TMD), and then to their use (or that of their derivatives) in emulsions in place of mycobacteria, so as to reduce the toxicity of these emulsions (Woodward L. F., 1990, Surface Chemistry and Classification of Vaccine Adjuvants and Vehicles, in Bacterial Vaccines, pp. 281–306, Alan R. Liss, New York).

The use of emulsions in vaccines has remained anecdotal for a long time; tests which were carried out, in man in particular, with, on the one hand, an influenza vaccine with an adjuvant of Freund incomplete type and, on the other hand, an emulsion containing groundnut oil, Arlacel A® and aluminum stearate, known under the name of "adjuvant 65", finally led to the banning of such formulae from human medicine.

The development on an industrial scale of water-in-oil emulsion vaccines had to await the work of Cessi and Nardelli (Develop. Biol. Standard., 1973, 25, 325–328). These vaccines were intended to protect laying hens against Newcastle disease, which is caused by a Paramyxovirus, throughout the whole period of egg laying; conventional vaccines, whose lower immunity was reflected by a fall in egg laying during passage of the virus through the poultry farm, were incapable of doing this. Vaccines of this type were quickly developed in the world of poultry farming, at least in Europe, for many avian diseases (for example infectious avian bronchitis, Gumboro disease). Emulsion-based vaccines, the emulsions being more particularly of oil-in-water type, for preventing many mammalian diseases, of bacterial origin (brucellosis in ruminants, enterotoxemia in ovines, colibacillosis) or viral origin (swine aphthous fever, swine influenza, Aujeszky's disease, and the like), also appeared on the market. However, although they generally have an immunogenic activity which is much greater than that of non-oily vaccines, these vaccines can cause local reactions at the injection site of the vaccine. These reactions, whose intensity depends on the formulation employed (water-in-oil or oil-in-water) and also on the nature of the antigens, are conventionally attributed to the presence of the mineral oil. In fact, the latter does not seem to be metabolized by the organism and in part remains close to the injection sites. It was therefore desirable to replace the mineral oil with a metabolizable oil.

Metabolizable oil must be understood to mean natural hydrocarbons present in nature, such as squalene, vegetable oils belonging to the category of triglycerides, semisynthetic triglycerides, such as triolein and medium-chain (C8/C10) triglycerides, fatty acid esters and more particularly oleyl oleates, propylene glycol dioleate or diesters of capric/ caprylic acids and propylene glycol.

At this stage, one difficulty is that the emulsions must be injectable and therefore fairly fluid; the result is to favor medium-chain triglycerides and certain esters, rather than vegetable oils, whose viscosity at 25° C. is already appreciable (50 to 70 mpa•s).

However, the major difficulty is to obtain stable water-in-oil emulsions with these oils and in particular vegetable oils. To do this, the use of monoglycerides is widespread in the food industry but, in general, the emulsions sought for and obtained are thick, which promotes their stability.

A number of emulsion formulae of water-in-oil type based on metabolizable oils have already been published: groundnut oil and lecithin (Brugh M. et al., Am. J. Vet. Res., 1983, 44, 72–75), oil enriched in modified phospholipids and diglycerides (Patent Application EP-A-0,417,562) and triglycerides or fatty esters in combination with hydrocarbons and with surface-active agents (French Patent No. 2,649, 013). None of these emulsion formulae corresponds to the present invention.

International Patent Application WO 91/00107 describes the preparation of emulsions from a mixture of metabolizable oil and non-metabolizable oil (from 2 to 95%) and emulsifying surface-active agents obtained by condensation of a liquid fatty acid at 20° C. with a sugar, such as mannitol, glucose or sucrose, or with glycerol. The surface-active agents chosen do not make it possible to produce an emulsion based solely on metabolizable oil.

Moreover, in Patent Application EP-A-0,174,377, polyglyceryl polyricinoleates were used as emulsifying agents in a very specific application for the preparation of water-oil-water double emulsions intended to have high resistance to heat, to freezing and to storage in the field of cosmetic and medical products for external use and conventional medicaments, for example insulin. The technical problem which this prior application was targeted at solving was especially that of preventing denaturation of the emulsion during final sterilization treatments or the like, which has no point in common with the search for adjuvant emulsions according to the invention.

We have surprisingly discovered that the use of polyglyceryl ricinoleate or of polyglyceryl polyricinoleate, alone or in combination with other surface-active agents such as monoglycerides, optionally hydrogenated polyoxyethylenated castor oils or else sorbitan esters, leads to fluid and very stable water-in-oil emulsions, both with, as oil, a triglyceride, which can be a vegetable oil or so-called medium-chain triglycerides (glyceryl tricaprylate/tricaprate), and propylene glycol esters (dioleate or else dicaprylate/dicaprate), or alternatively esters of oleyl or decyl oleate type. These water-in-oil emulsions have an adjuvant power. These formulae can validly be extended to natural hydrocarbons, for example squalene.

Moreover, we have discovered that certain surface-active agents belonging to the optionally hydrogenated polyoxyethylenated castor oil series lead, with certain oils, and more particularly with certain esters of oleic acid (especially with oleyl alcohol or propylene glycol), to water-in-oil emulsions which are very stable, are fluid at 4° C. and have an adjuvant power.

High stability within the meaning of the present invention is understood to mean a stability which is reflected by a homogeneous macroscopic appearance, for example to the naked eye, for a period of time compatible with the possible period of storage of the product or vaccine containing the emulsion, which duration is preferably of a number of months and which can be greater than one year.

It has thus become possible to produce emulsions based on metabolizable oils which are extremely stable and have a high adjuvant power, while having excellent tolerance, and which are fluid at low temperature, especially at 4° C.

The subject of the present invention is therefore an injectable water-in-oil emulsion which combines, for the first time, the exclusive use of metabolizable oil, which makes it possible to obtain very good tolerance, and the production of a stable emulsion which has the fluidity required to enable it to be administered by injection, as well as an immunity adjuvant nature. With respect to the emulsions of the prior art, of the type containing an oily phase with an emulsifying agent or emulsifying surface-active agent, the emulsion according to the invention is characterized in that the oil of the oily phase is a metabolizable oil or a mixture of metabolizable oils and the emulsifying agent, or mixture of emulsifying agents, is suitable for obtaining, with the metabolizable oil, a stable emulsion which has a relatively low viscosity (less than 400 mpa•s at 25° C.) and which advantageously remains fluid at 4° C.

The emulsifying agent or emulsifying surface-active agent is preferably based on ricinoleic acid ester and/or polyglyceryl ester. As will be seen later, certain surface-active agents according to the invention are simultaneously polyglyceryl esters and ricinoleic acid esters. These are especially polyglyceryl polyricinoleates and ricinoleates. It is understood that the invention relates to the discovery that these surface-active agents make it possible to use only metabolizable oils and that these surface-active agents can advantageously or even preferentially be employed in the presence of other conventional surface-active agents.

The metabolizable oily phase can consist of natural hydrocarbons, for example squalane (2,6,10,15,19,23-hexamethyltetracosane), squalene (2,6,10,15,19,23-hexamethyl-2,6,10,14,18,22-tetracosahexaene) or pristane (2,6,10,14-tetramethylpentadecane).

The metabolizable oily phase can advantageously consist of vegetable oil, preferably from the triacylglycerol series, especially sunflower, soya, maize or sweet almond oil.

The metabolizable oily phase can alternatively advantageously and even preferentially consist of esters of natural fatty acids and of alcohols.

The alcohols can be, alone or as a mixture:

polyols such as pentaerythritol but more particularly glycerol and/or propylene glycol (also known as 1,2-propanediol);

linear-chain aliphatic monoalcohols, such as isopropanol and primary alcohols, such as ethanol, butanol, 1-octanol, 1-decanol and more particularly oleyl alcohol (or 9-octadecen-1-ol);

branched-chain aliphatic monoalcohols, such as 2-ethyl-1-hexanol and so-called isocetyl alcohol.

Most of the fatty acids are preferably natural, C6 to C24, fatty acids, preferably oleic and/or linoleic acid or capric and/or caprylic acid.

Most of the fatty acids can also be diacids such as succinic acid or adipic acid or else branched fatty acids and more particularly isostearic acid.

Preference is especially given, among the various esters, to oleyl oleates or propylene glycol diesters, more particularly propylene glycol dioleate or dicaprate/dicaprylate.

In a first preferred embodiment, the emulsifying surface-active agents contain, in all or in part, polyglyceryl esters in a final proportion of 0.4 to 20% w/v, preferably between 1 and 10% and more particularly between 3 and 5% w/v.

The polyglyceryl esters can be, in all or in part, esters of polyglycerol and of natural fatty acids, such as oleic acid, stearic acid or ricinoleic acid, or else of branched fatty acids such as isostearic acid.

The polyglyceryl esters can be, in all or in part, polyglyceryl ricinoleates (12-hydroxy-9-octadecenoate).

For example, the polyglyceryl esters are, in all or in part, polyglyceryl polyricinoleates.

The polyglycerol advantageously has from 2 to 12 glycerol residues and more particularly from 2 to 5 residues.

The polyglyceryl ester can be combined with other surface-active agents, in particular sorbitan oleate, optionally hydrogenated polyoxyethylenated castor oils (see later the castor oils according to the invention) and/or natural surface-active agents. The polyglyceryl ester can specifically be associated, in a small amount, with other surface-active agents, especially castor oils according to the invention, in particular at a concentration of less than 1% w/v, especially of the order of 0.4 to 1% w/v.

The natural surface-active agents are, for example, lecithin or else (mono+di) glycerides, more particularly glycerides of unsaturated fatty acids (mostly oleic and/or linoleic) and of medium-chain fatty acids (caprylic and/or capric).

In another preferred embodiment, the emulsifying surface-active agents comprise, in all or in part, optionally hydrogenated polyoxyethylenated castor oils. This or these polyoxyethylenated castor oil(s) is/are preferably in a final proportion of 0.5 to 25% w/v, preferably between 2 and 10% and more particularly between 4 and 8%.

The optionally hydrogenated polyoxyethylenated castor oils advantageously have a degree of ethoxylation of less than 18 mol of ethylene oxide per mole.

The optionally hydrogenated polyoxyethylenated castor oils can be combined with one another and/or with other surface-active agents belonging to different chemical series, in particular sorbitan derivatives, polyoxyethylenated fatty acids or alcohols, glycerides or lecithins. As was seen above, the castor oils can also be combined with the polyglyceryl esters according to the invention and generally with all the surface-active agents indicated in the first embodiment.

The aqueous phase of the emulsion is advantageously in a proportion such that the viscosity of the emulsion is acceptable, so that the said emulsion can be easily injected, preferably between 5 and 50% and more particularly between 12 and 25% v/v.

The emulsion can contain immunity-modulating substances.

The invention also relates to the vaccines formed from an emulsion according to the invention and characterized in that the aqueous phase of the emulsion according to the invention contains, alone or in combination, complete antigens of viral, bacterial or parasitic origin or else fractions of the said antigens or proteins obtained by genetic recombination.

It also relates to the immunological medicaments characterized in that the aqueous phase of the emulsion according to the invention contains a foreign protein or a modified protein or a hapten conjugated to a carrier molecule.

The invention also, of course, relates to the processes for the preparation of the emulsions, vaccines and immunological medicaments described hereinabove which consist in bringing the constituents together in an appropriate way and emulsifying.

A further subject of the invention is the use of the polyglyceryl esters and ricinoleic acid esters according to the invention for preparing water-in-oil emulsions which have adjuvant activity, which are stable, which have a relatively low viscosity and which comprise an oily phase mostly made up of metabolizable oil but containing a minor amount of non-metabolizable oil.

A few examples of formulae and their properties will be given hereinbelow by way of illustration of the present invention. It is obvious, for those skilled in the art, that the phase proportions and the concentrations of surface-active agents which have been used in the examples hereinbelow can extend over a much larger range of variation. Likewise, those skilled in the art are able to prepare and test, in the usual way, any combination of a conventional surface-active agent and of a surface-active agent according to the invention.

Example No. 1

This example is intended to illustrate the effectiveness of the polyglyceryl polyricinoleates as surface-active agents.

200 ml of isotonic buffer are emulsified in 800 ml of oleyl oleate (Cetiol, Henkel) containing 5% w/v of polyglyceryl polyricinoleate (Radiamuls 2253, Oléofina) using a turbine emulsifier (Silverson).

The emulsion obtained is very stable (beginning of settling but no trace of continuous aqueous phase after 1 year at 4° C., as well as at room temperature) and fluid (170 mpa•s at 4° C., 60 mPa•s at 25° C.).

The use of sweet almond oil in place of oleyl oleate also leads to a water-in-oil emulsion which is stable at 4° C. as well as at room temperature and which is relatively fluid (360 mpa•s at 5° C., 140 mpa•s at 25° C.).

Soya oil also leads to a stable emulsion, as do medium-chain (C8–C10) triglycerides and diesters of propylene glycol (oleic or else caprylic/capric).

Example No. 2

This example is intended to illustrate the surface-active properties of Arlacel 1689 (ICI) which contains polyglyceryl-3 ricinoleate and sorbitan oleate. 35 ml of aqueous phase consisting of an isotonic buffer containing antigen are emulsified, using a turbine emulsifier (Silverson), in 140 ml of oily phase formed of a 5% (w/v) solution of Arlacel 1689 (ICI) in the oil, the oil being, without distinction, either oleyl oleate, sweet almond oil, sunflower oil or medium-chain triglycerides.

The four emulsions prepared with the various oils are all stable and fluid at 4° C.

Example No. 3

This example is intended to illustrate the preparation of stable water-in-oil emulsions with polyoxyethylenated hydrogenated castor oil as surface-active agent.

200 ml of isotonic buffer are emulsified, using a turbine emulsifier (Silverson), in 800 ml of oleyl oleate (Cétiol, Henkel) containing 5% w/v of polyoxyethylenated (7 EO) hydrogenated castor oil (Dehymuls HRE7, Henkel).

The emulsion obtained is stable at 4° C. (no break after more than one year) and fluid (60 mPa•s at 25° C.).

The use of propylene glycol dioleate (Radia 7204, Oléofina) in place of oleyl oleate leads to the same result. With propylene glycol dioleate, for example, it is possible to employ polyoxyethylenated castor oils containing, per mole, 5 ethylene oxide residues (Etocas 5, Croda) to 9 residues (Acconon CA-9, Karlshamns).

However, the emulsions prepared under the same conditions with triglycerides (vegetable oils or else tricaprylate/tricaprate) in the absence of co-surface-active agent are not stable. Moreover, certain polyoxyethylenated castor oils do not lead alone to stable water-in-oil emulsions and it will be preferable to employ them in accordance with the invention in combination with other conventional surface-active agents or surface-active agents according to the invention.

Example No. 4

This example is intended to demonstrate the influence of the concentration of polyglyceryl polyricinoleate on the stability of the emulsions.

Emulsions were prepared with 80% v/v of oily phase (oleyl oleate) containing from 1 to 8% (w/v) of polyglyceryl polyricinoleate. After three months at 4° C., those containing from 3 to 8% (w/v) of surface-active agent in the oily phase are more particularly stable.

The same result is obtained by replacing oleyl oleate with sweet almond oil.

Example No. 5

This example is intended to show the possibility of combining a polyglyceryl polyricinoleate with a monoglyceride.

Two oily phases, one containing 5% (w/v) of polyglyceryl polyricinoleate (Radiamuls 2253, Oleofina) in sweet almond oil and the other containing 5% (w/v) of glyceryl monooleate (Radiasurf 7150, Oléofina) in sweet almond oil, are mixed in variable proportions. 40 ml of aqueous phase are then emulsified in 160 ml of each of the different oily phases prepared, using a turbine emulsifier (Silverson). While the emulsion containing only glyceryl monooleate becomes heterogeneous, indeed breaks up, in a few days, those containing a final Radiamuls 2253 content of at least 1.6% are stable at 4° C. and at room temperature. The formula containing a final content of 2% of each of the 2 surface-active agents has a viscosity of 130 mpa•s at 25° C.

Example No. 6

This example is intended to show the possibility of combining a polyglyceryl polyricinoleate with a polyoxyethylenated castor oil.

The conditions are the same as in Example 5 but, in this instance, the oil is soya oil and one of the two phases contains, in place of glyceryl monooleate, hydrogenated castor oil polyoxyethylenated with 7 EO (Dehymuls HRE 7, Henkel). The emulsions containing a final Radiamuls 2253 content of at least 1.6% are stable at 4° C. and at room temperature. The viscosity, for an emulsion containing a final Radiamuls 2253 content of 1.6%, is 120 mpa•s at 25° C.

What is claimed is:

1. Vaccine or immunological medicament comprising a water-in-oil emulsion to enhance the immunological response, said emulsion comprising:
   (a) an aqueous phase containing a vaccinal antigen or an immunologically active ingredient; and
   (b) an oily phase comprising a metabolizable oil and an emulsifier selected from the group consisting of ricinoleic acid ester, polyglyceryl ester, polyoxyethylenated castor oil, and mixtures thereof;
   wherein the emulsion has a viscosity of less than 400 mpa•s at 25° C.

2. Vaccine on immunological medicament according to claim 1, wherein the polyglyceryl esters are, in all or in part, esters of polyglycerol and natural fatty acids, or branched fatty acids.

3. Vaccine on immunological medicament according to claim 2 wherein the natural fatty acids are selected from the group consisting of oleic acid, stearic acid and ricinoleic acid.

4. Vaccine on immunological medicament according to claim 2 wherein the branched fatty acid is isostearic acid.

5. Vaccine on immunological medicament according to claim 1, wherein the polyglyceryl esters are, in all or in part, polyglyceryl polyricinoleates or ricinoleates.

6. Vaccine on immunological medicament according to claim 1, wherein the polyglycerol has from 2 to 12 glycerol residues and more particularly from 2 to 5 residues.

7. Vaccine or immunological medicament according to claim 1 wherein the emulsifier is combined with other emulsifiers.

8. Vaccine on immunological medicament according to claim 7, wherein said other emulsifiers are selected from the group consisting of lecithin and mono+di glycerides.

9. Vaccine or immunological medicament according to claim 1, wherein the emulsion comprises an optionally hydrogenated polyoxyethylenated castor oil.

10. Vaccine on immunological medicament according to claim 9, wherein the castor oil is in a final proportion of 0.5 to 25% w/v, preferably between 2 and 10% and more partculary between 4 and 8%.

11. Vaccine on immunological medicament according to claim 9, whereine the optionally hydrogenated polyoxyethylenated castor oils have a degree of ethoxylation which is less than 18 mol of ethylene oxide per mole.

12. The vaccine or immunological medicament according to claim 9 wherein the polyoxyethylenated castor oil has a degree of ethoxylation which is less than 18 mol of ethylene oxide per mole.

13. Vaccine on immunological medicament according to claim 1, wherein the metabolizable oily phase consists of natural hydrocarbons.

14. Vaccine on immunological medicament according to claim 4, wherein the metabolizable oily phase consists of vegetable oil of the triacylglycerol series.

15. Vaccine on immunological medicament according to claim 1, wherein the metabolizable oily phase consists of esters of fatty acids and of alcohols.

16. Vaccine on immunological medicament according to claim 15, wherein the alcohols of the esters are, alone or as a mixture:
   polyols;
   linear-chain aliphatic monoalcohols;
   branched-chain aliphatic monoalcohols.

17. Vaccine on immunological medicament according to claim 16 wherein
   the polyols are selected from the group consisting of pentaerythritol, glycerol and propylene glycol;
   the linear chain aliphatic monoalcohols are selected from the group consisting of ethanol, butanol, 1-octanoly-1-decanol, oleyl alcohol and isopropanol;
   the branched-chain aliphatic monoalcohols are selected from the group consisting of 2-ethyl-1-hexanol and isocetyl alcohol.

18. The vaccine or immunological medicament according to claim 16 wherein the fatty acids comprise natural acids of 6 to 20 carbons.

19. The vaccine or immunological medicament according to claim 18 wherein the fatty acids are selected from the group consisting of oleic acid, linoleic acid, capric acid, caprylic acid, and mixtures thereof.

20. The vaccine or immunological medicament according to claim 16 wherein the fatty acids comprise diacids or branched fatty acids.

21. The vaccine or immunological medicament according to claim 20 wherein the fatty acids are selected from the group consisting of succinic acid, adipic acid, isostearic acid, and mixtures thereof.

22. Vaccine on immunological medicament according to claim 15, wherein most of the fatty acids entering into the composition of the esters are natural acids of 6 to 24 carbons.

23. Vaccine on immunological medicament according to claim 15, most of the fatty acids entering into the composition of the esters are diacids.

24. Vaccine according to claim 1, characterized in that the aqueous phase of the emulsion contains, alone or in combination, complete antigens of viral, bacterial or parasitic origin, or else fractions of the said antigens, or proteins obtained by genetic recombination.

25. Immunological medicament according to claim 1, wherein the aqueous phase contains a foreign protein or a modified protein or a hapten conjugated to a carrier molecule.

26. Emulsion according to claim 1, wherein the aqueous phase of the emulsion is in a proportion of between 5 and 50% with respect to the whole emulsion.

27. Emulsion according to claim 1, wherein the aqueous phase of the emulsion is in a proportion of between 12 and 25% VN with respect to the whole emulsion.

28. Vaccine or immunological medicament according to claim 1, wherein the emulsifier comprises a polyglyceryl ester which is an ester of polyglycerol and isostearic acid.

29. Vaccine or immunological medicament according to claim 1, wherein the emulsifier comprises optionally hydrogenated, polyoxyethylenated castor oil and an ester of polyglycerol and a natural fatty acid or a branched fatty acid.

30. Vaccine or immunological medicament according to claim 29, wherein the natural fatty acids are selected from the group consisting of oleic acid, stearic acid and ricinoleic acid.

31. Vaccine or immunological medicament according to claim 29, wherein the branched fatty acid is isostearic acid.

32. Vaccine or immunological medicament according to claim 1, wherein the emulsifier comprises optionally hydrogenated, polyoxyethylenated castor oil and an ester of polygylcerol and isostearic acid.

33. Vaccine or immunological medicament according to claim 1, wherein the emulsifier comprises optionally hydrogenated, polyoxyethylenated castor oil and an ester of polyglycerol and polyricinoleate or ricinoleate acid.

34. The vaccine or immunological medicament according to claim 1 wherein the emulsifier comprises a polyglyceryl ester.

35. The vaccine or immunological medicament according to claim 1 wherein the emulsifier comprises a ricinoleic acid ester.

36. The vaccine or immunological medicament according to claim 35 wherein the ricinoleic acid ester comprises polyglyceryl polyricinoleate or ricinoleate.

37. The vaccine or immunological medicament according to claim 1 wherein the polyoxyethylenated castor oil has a degree of ethoxylation which is less than 18 mol of ethylene oxide per mole.

38. The vaccine or immunological medicament according to claim 1 wherein the emulsifier comprises a polyglyceryl ester in a final proportion of 0.4 to 20% w/v.

39. The vaccine or immunological medicament according to claim 38 wherein the emulsifier comprises a polyglyceryl ester in a final proportion of 1 to 10% wlv.

40. The vaccine or immunological medicament according to claim 38 wherein the emulsifier comprises a polyglyceryl ester in a final proportion of 3 to 5% wlv.

41. The vaccine or immunological medicament according to any one of claims 1–23 and 26–40 wherein the oil present in the emulsion consists of a metabolizable oil.

* * * * *

UNITED STATES PATENT AND TRADEMARK OFFICE
CERTIFICATE OF CORRECTION

PATENT NO. : 6,235,282 B1
DATED : May 22, 2001
INVENTOR(S) : Riviere et al.

It is certified that error appears in the above-identified patent and that said Letters Patent is hereby corrected as shown below:

<u>Title page,</u>
Item [73], Assignee: should read -- MERIAL, Lyon (FR) --

Signed and Sealed this

Eighteenth Day of June, 2002

*Attest:*

*Attesting Officer*

JAMES E. ROGAN
*Director of the United States Patent and Trademark Office*